(12) United States Patent
Cho et al.

(10) Patent No.: US 6,520,272 B2
(45) Date of Patent: Feb. 18, 2003

(54) MICRO ROBOT

(75) Inventors: Kyung-il Cho, Seoul (KR); Sang-eun Baek, Yongin (KR)

(73) Assignee: Samsung Electronics Co., Ltd. (KR)

( * ) Notice: Subject to any disclaimer, the term of this patent is extended or adjusted under 35 U.S.C. 154(b) by 8 days.

(21) Appl. No.: 09/911,383

(22) Filed: Jul. 25, 2001

(65) Prior Publication Data

US 2002/0029915 A1 Mar. 14, 2002

(30) Foreign Application Priority Data

Jul. 25, 2000 (KR) .......................................... 00-42747

(51) Int. Cl.$^7$ .............................................. B62D 51/06
(52) U.S. Cl. ....................................... 180/8.1; 180/8.6
(58) Field of Search .......................... 180/7.1, 8.1, 8.6

(56) References Cited

U.S. PATENT DOCUMENTS

| | | | |
|---|---|---|---|
| 2,914,127 A | * 11/1959 | Ricouard | 180/8.5 |
| 3,537,540 A | * 11/1970 | Zuppiger | 180/8.1 |
| 3,680,489 A | * 8/1972 | English | 104/23.2 |
| 3,807,519 A | * 4/1974 | Patch | 180/8.5 |
| 3,831,691 A | * 8/1974 | Jenkins | 180/119 |
| 3,985,064 A | * 10/1976 | Johnson | 198/630 |
| 4,227,608 A | * 10/1980 | Alfthan et al. | 180/8.1 |
| 4,462,476 A | * 7/1984 | Shkolnik | 180/8.6 |
| 4,674,949 A | * 6/1987 | Kroczynski | 114/222 |
| 4,894,579 A | * 1/1990 | Higuchi et al. | 310/328 |
| 5,096,009 A | * 3/1992 | Hirmann | 180/7.1 |
| 5,161,631 A | * 11/1992 | Urakami | 180/164 |
| 5,351,626 A | * 10/1994 | Yanagisawa | 180/164 |
| 5,372,211 A | * 12/1994 | Wilcox et al. | 180/8.2 |
| 5,513,016 A | * 4/1996 | Inoue | 358/3.26 |
| 5,762,152 A | * 6/1998 | Foster et al. | 180/8.5 |
| 5,788,002 A | * 8/1998 | Richter | 180/8.1 |
| 5,821,666 A | * 10/1998 | Matsumoto et al. | 310/316.01 |
| 6,069,420 A | * 5/2000 | Mizzi et al. | 310/15 |
| 6,267,191 B1 | * 7/2001 | Hettinger | 180/187 |

OTHER PUBLICATIONS

US 2002/0111535 A1, Kim et al., Aug. 15, 2002, US patent application Publication.*

* cited by examiner

*Primary Examiner*—Kevin Hurley
*Assistant Examiner*—Paul Royal, Jr.
(74) *Attorney, Agent, or Firm*—Burns Doane Swecker & Mathis, LLP

(57) ABSTRACT

A micro robot includes first and second masses, each having a first contact surface having a first frictional coefficient and a second contact surface having a second frictional coefficient and formed to be inclined by a predetermined angle with respect to the first contact surface, the first and second contact surfaces being formed at the lower portion of the mass corresponding to a surface of a target object, and an actuator provided between the first and second masses for periodically changing the distance between the first and second masses and enabling the first and second contact surfaces of the first and second masses to selectively contact the surface of the target object in synchronization with a periodic change in distance between the first and second masses. Thus, the micro robot is moved by the change in the distance between the masses constituting the micro robot together with the periodic change in friction between each of the masses and the surface of the object on which the micro robot moves, instead of using wheels or caterpillar tracks. Thus, the protective cover can protect the power source.

18 Claims, 4 Drawing Sheets

MICRO ROBOT

The present application is based upon Korean Application 2000-42747 filed in the Republic of Korea on Jul. 25, 2000, herein incorporated by reference.

BACKGROUND OF THE INVENTION

1. Field of the Invention

The present invention relates to a micro robot, and more particularly, to a micro robot that has a simple structure and is protected from erosive materials.

2. Description of the Related Art

Presently, to perform a stomach treatment using an endoscope, air is injected into a portion to be examined and a rigid hose is inserted through a path into the expanded stomach, so that the inside of the stomach is examined. Here, a patient feels severe pain due to pressure and friction at portions of the stomach the rigid hose contacts. To relieve the patient's pain, a micro robot for a stomach endoscope has been developed. The micro robot that is slightly larger than an average sized pill is swallowed by a patient who is lying on a bed. The micro robot is moved back and forth by means of wireless control, so that the intestines of the patient can be examined. Here, it is most required to develop an operation mechanism for enabling the micro robot to move back and forth. Since various secretions inside the intestines of a human body are detrimental to parts of the micro robot, sealing of the robot is necessary. Also, the structure of the robot must be simple since many actuators cannot be installed in a micro robot.

However, a typical robot uses a plurality of wheels or caterpillar tracks as a means for moving. The wheels or caterpillar tracks and a power transferring mechanism for driving them, are unavoidably exposed outside the robot. Thus, the driving mechanism comes in contact with the secretions of the intestines of a human body and can be easily corroded, and further the robot is not able to effectively move inside the intestines. To prevent the above problems, the wheels or caterpillar tracks, and the power transferring mechanism for driving them must be sealed for protection from secretions. However, when the wheels or caterpillar tracks are sealed, their function as a position moving means is lost. If the wheels or caterpillar tracks are exposed outside and only the power transferring mechanism is sealed, the structure of the robot becomes complicated and damage to the wheels or caterpillar tracks is unavoidable.

One way to solve the above problems is to apply an active sucker to a body of the robot. In this case, since miniaturation of the active sucker and a power source for driving the active sucker is difficult, manufacturing of the active sucker and the power source is not easy. Furthermore, although a driving force in one direction can be provided to a robot, providing a driving force in two opposite-directions (forward and backward) is difficult due to the characteristics of the robot.

SUMMARY OF THE INVENTION

To solve the above problems, it is a first objective of the present invention to provide a micro robot having a structure by which it can be protected from corrosive materials.

It is a second objective of the present invention to provide a micro robot having a simple structure so that it can be miniaturized.

Accordingly, to achieve the above objectives, there is provided a micro robot includes first and second masses, each having a first contact surface having a first frictional coefficient and a second contact surface having a second frictional coefficient and formed to be inclined by a predetermined angle with respect to the first contact surface, the first and second contact surfaces being formed at the lower portion of the mass corresponding to a surface of a target object, and an actuator provided between the first and second masses for periodically changing the distance between the first and second masses and enabling the first and second contact surfaces of the first and second masses to selectively contact the surface of the target object in synchronization with a periodic change in distance between the first and second masses.

It is preferred in the present invention that each of the first and second masses has four side surfaces and the first and second contact surfaces are provided at the lower portion of each of the first and second masses. In particular, it is preferred in the present invention that each of the first and second masses has four side surfaces and the first and second contact surfaces are provided at both the upper and lower portions of each of the first and second masses.

It is preferred in the present invention that the first frictional coefficient is higher than the second frictional coefficient, and the first contact surfaces of the first and second masses each having the first frictional coefficient are arranged close to the actuator while the second contact surfaces of the first and second masses are arranged next to the first contact surfaces and farther out from the actuator.

It is preferred in the present invention that the actuator comprises a motor, a crank having first and second crank portions located at opposite sides of the center of rotation along arbitrary axes parallel to each other, first and second arms rotatably connected to the first and second crank portions of the crank and fixedly coupled to the surfaces of the first and second masses facing the actuator, and a plurality of gears transferring power of the motor.

In particular, it is preferred in the present invention that a protective cover for protecting the actuator is provided between the first and second masses.

BRIEF DESCRIPTION OF THE DRAWINGS

The above objectives and advantages of the present invention will become more apparent by describing in detail a preferred embodiment thereof with reference to the attached drawings in which.

DETAILED DESCRIPTION OF THE INVENTION

Figure 1:
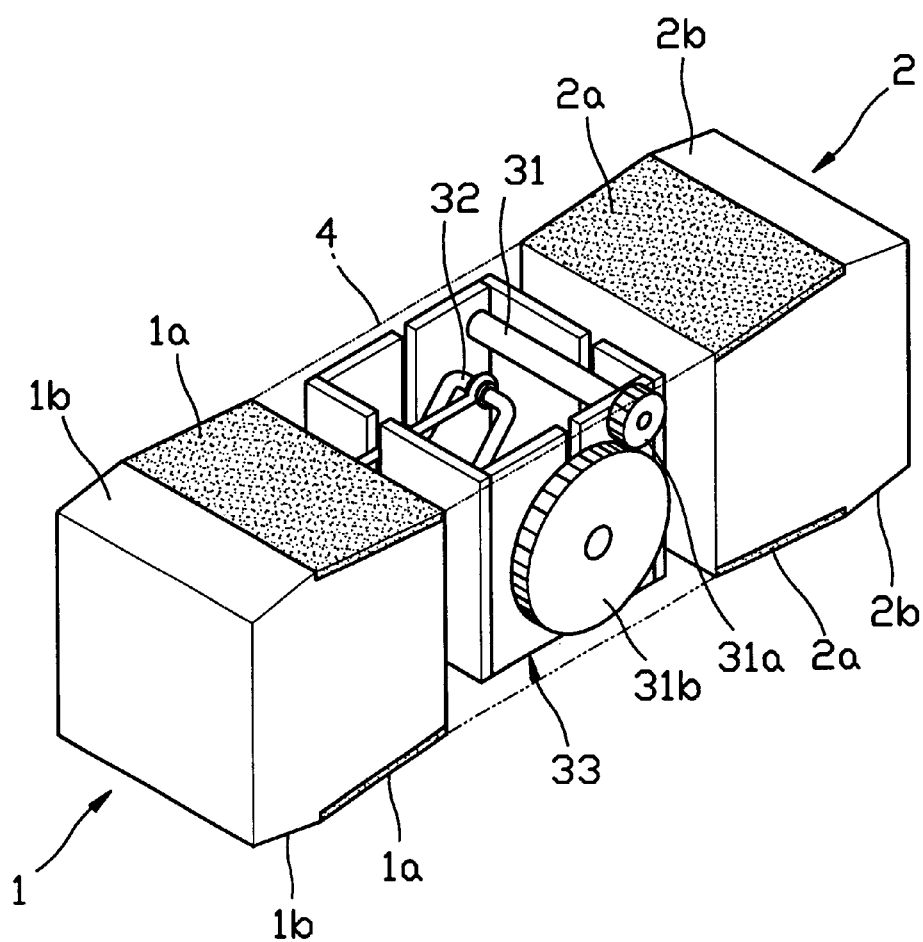
FIG. 1 is a perspective view showing a micro robot according to a preferred embodiment of the present invention.
Figure 2:
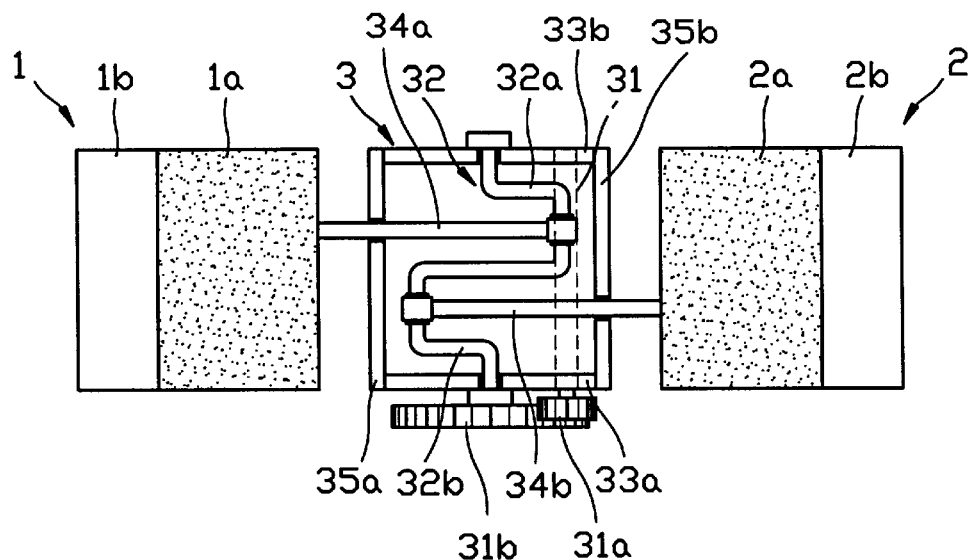
FIG. 2 is a plan view of the micro robot of FIG. 1.
Figure 3:
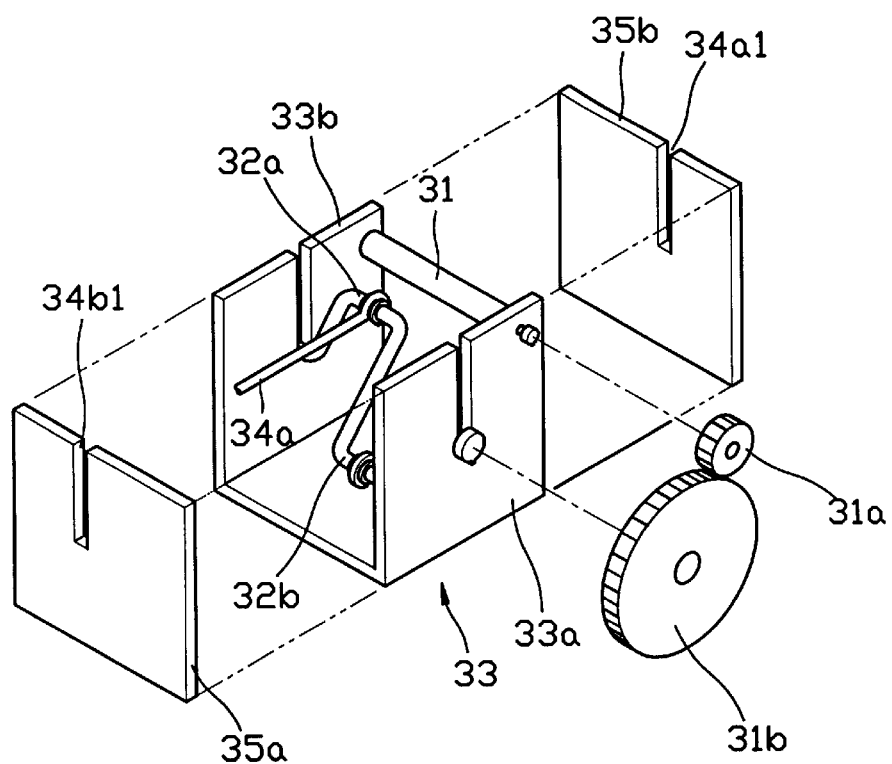
FIG. 3 is a perspective view showing an actuator applied to the micro robot of FIG. 1.

Referring to FIGS. 1 through 3, a first mass 1 and a second mass 2 are linearly aligned in one direction with respect to an actuator 3. The upper and lower surfaces of each of the first and second masses 1 and 2 are formed to be symmetrical. First contact surfaces 1a and 2a which are inclined and second contact surfaces 1b and 2b are formed on the first and second masses 1 and 2. Also, the first and second masses 1 and 2 are arranged such that the first contact surface 1a and the second contact surface 2a can face each other.

To protect a motor and other related motor devices that will be described later, the actuator 3 between the first mass 1 and the second mass 2 may be covered with a protective cover 4 which is formed of a soft material. Preferably, the protective cover 4 is flexible such that it does not prevent the motion of the actuator 3, and resistant to corrosion caused by any outside materials contacting the protective cover 4. Also, it is preferable that the protective cover 4 is flexibly wrinkled so that the protective cover 4 can adapt to a change in distance between and relative orientation of the first and second masses 1 and 2.

In the first and second masses 1 and 2, the first contact surfaces 1a and 2a each have a first frictional coefficient while the second contact surfaces 1b and 2b each have a second frictional coefficient which is lower than the first frictional coefficient.

The actuator 3 provided between the first and second masses 1 and 2 periodically changes the distance between the first and second masses 1 and 2. In synchronization with a periodic change in the distance between the first and second masses 1 and 2, the first contact surfaces 1a and 2a and the second contact surfaces 1b and 2b of the first and second masses 1 and 2 selectively contact the surface of an object on which the micro robot moves.

In the actuator 3, there is a micro motor 31, a crank 32 rotated by the micro motor 31, arms 34a and 34b for connecting the first and second masses 1 and 2 to the crank 32, and first and second gears 31a and 31b for transferred a rotation force from the micro motor 31 to the crank 32.

The first gear 31a is connected to a rotation shaft of the micro motor 31. The second gear 31b is engaged with the first gear 31a and connected to the crank 32. The parts of the actuator 3 are supported by a U-shape frame 33. The U-shape frame 33 has first and second extending portions 33a and 33b parallel to each other. The crank 32 is disposed between the first and second extending portions 33a and 33b. Both ends of the crank 32 are rotatably supported by the first and second extending portions 33a and 33b. The second gear 31b is provided outside the first extending portion 33a and fixed to one end of the crank 32 supported by the first extending portion 33a.

The micro motor 31 is supported at the upper portions of the first and second extending portions 33a and 33b. The first gear 31a engaged with the second gear 31b is fixed to one end of the rotation shaft of the micro motor 31.

The first and second arms 34a and 34b coupled to the crank 32 are firmly fixed to the side surfaces of the first and second masses 1 and 2. The crank 32 includes first and second crank portions 32a and 32b arranged to be symmetrical with respect to the center of rotation and maintaining a constant distance from the center of rotation. One end of each of the first and second arms 34a and 34b is rotatably coupled to each of the first and second crank portions 32a and 32b.

First and second plates 35a and 35b for guiding the motion of the first and second arms 34a and 34b are disposed at both sides of the frame 33 facing the first and second masses 1 and 2. Guide slots 34a1 and 34b1 for restricting the first and second arms 34a and 34b to move only up and down are formed in the first and second plates 35a and 35b, respectively.

Figure 4:
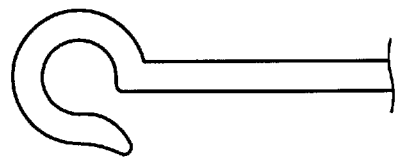
FIG. 4 shows an arm applied to the actuator of FIG. 3 in the micro robot according to the present invention.
Figure 5:
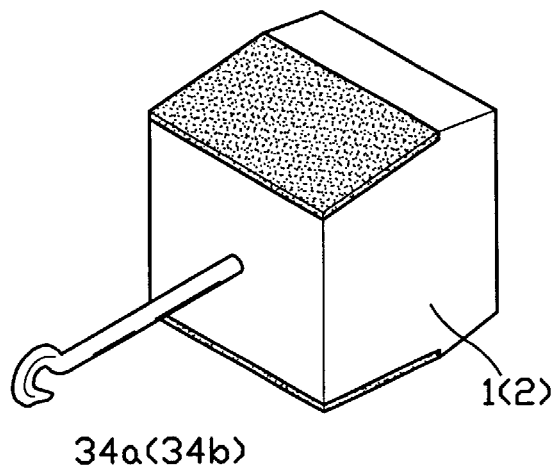
FIG. 5 is a perspective view showing the arm and a crank portion applied to the actuator of FIG. 3 in the micro robot according to the present invention.

One end portion of each of the first and second arms 34a and 34b is formed to have a hook shape, as shown in FIG. 4, so that they can be hooked to the first and second crank portions 32a and 32b. The other end portions of the first and second arms 34a and 34b are fixed at the side surfaces of the first and second masses 1 and 2.

Figure 6:
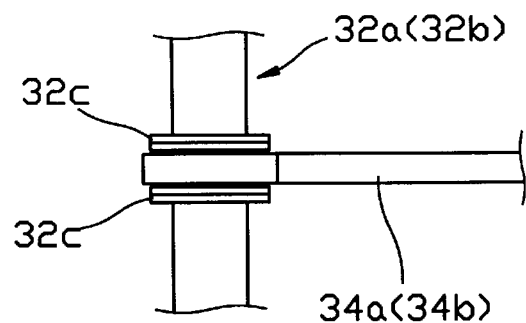
FIG. 6 is a plan view showing a crank portion and the arm connected to the crank in the micro robot of FIG. 1.

Also, as shown in FIG. 6, movement prevention washers 32c for supporting the hook portions of the first and second arms 34a and 34b are coupled to the first and second crank portions 32a and 32b where the hooks of the first and second arms 34a and 34b are coupled.

The micro robot having the above structure according to the present invention can move as the distance between the first and second masses 1 and 2 is changed and the first contact surfaces 1a and 2a and the second contact surfaces 1b and 2b are made to selectively contact the surface of a target object, by the actuator 3 having the above structure.

The operation of the micro robot according to the present invention is described with reference to the accompanying drawings. FIGS. 7A through 7E show a sequence of the motion of the micro robot according to the present invention.

Figure 7A:
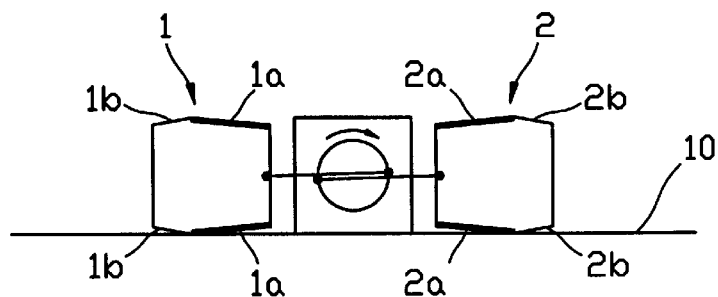
FIGS. 7A thorugh 7E are views showing the principle of motion of the micro robot according to the present invention.
Figure 7B:
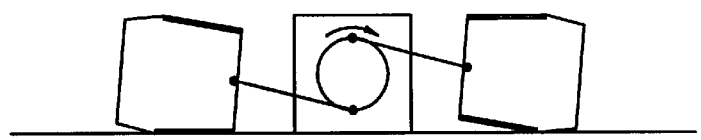

In FIG. 7A, the first and second masses 1 and 2 are located close to each other and the first and second arms 34a and 34b overlap due to the position of the crank 32. Here, not the first and second contact surfaces 1a, 2a, 1b, and 2b of the first and second masses 1 and 2, but an edge portion between the contact surfaces 1a and 1b and an edge portion between the contact surfaces 2a and 2b, contact the surface 10 of a target object. In this state, the crank 32 rotates clockwise by 90°, as shown in FIG. 7B. Here, the distance between the first and second masses 1 and 2 and the posture of each of the first and second masses 1 and 2 are changed. Here, it is assumed that there is less friction between the bottom of the actuator 3 and the surface 10 of a target object than between the first contact surfaces 1a and 2a of the first and second masses 1 and 2 and the surface 10 of the target object.

Referring to FIG. 7B, the first contact surface 1a of the first mass 1 and the second contact surface 2b of the second mass 2 contact the surface 10 of the target object. Here, the distance between the first and second masses 1 and 2 is wider compared to the state shown in FIG. 7A. As can be seen in FIG. 7B, the first contact surface 1a of the first mass 1 and the second contact surface 2b of the second mass 2 are completely in contact with the surface 10 of the target object. In detail, as the micro robot begins to move from the state of FIG. 7A to the state of FIG. 7B, the first contact surface 1a of the first mass 1 and the second contact surface 2b of the second mass 2 start to contact the surface 10 of the target object while the distance between the first and second masses 1 and 2 gradually increases. The first contact surface 1a of the first mass 1 which has a relatively stronger friction force contacts the surface 10 of the target object while the second contact surface 2b of the second mass 2 which has a relatively weaker frictional force contacts the surface 10. Here, since the distance between the first and second masses 1 and 2 is wide, forces to push the first and second masses 1 and 2 to move outside with respect to the actuator 3 are generated. However, since the first contact surface 1a of the first mass 1 having a relatively stronger frictional force is in contact with the surface 10, the first mass 1 does not move. As a result, the second contact surface 2b of the second mass 2 having a relatively weaker frictional force is moved in one direction (to the right on the drawing sheet) due to the first mass 1 standing still, as shown in FIG. 7B.

Figure 7C:
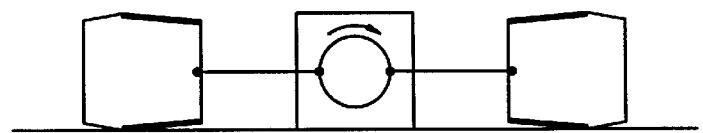

When the crank 32 further rotates clockwise by 90°, thus rotating 180° from the original state, the first and second masses 1 and 2 are spaced apart from the actuator 3 and from each other by the maximum distance so that not the first and second contact surfaces 1a, 2a, 1b, and 2b, but the boundary portions between the contact surfaces of each of the first and second masses 1 and 2, that is, the edge portions, contact the surface 10 of the target object. Before the first and second masses 1 and 2 move to the positions as shown in FIG. 7C, as the crank 32 rotates, the first contact surface 1a having a strong frictional force maintains a partial contact state with respect to the surface 10 of the target object. Simultaneously, since the second contact surface 2a of the second mass 2 having a relatively weaker frictional force maintains a partial contact state with respect to the surface 10, the second mass 2 further moves as shown in FIG. 7C.

Figure 7D:
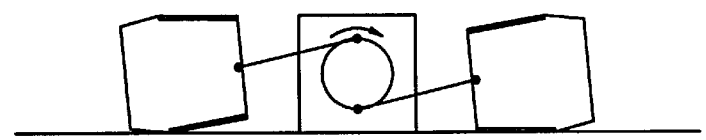

Next, when the crank 32 further moves clockwise by 90°, thus rotating 270° from the original state, as shown in FIG. 7D, the distance between the first and second masses 1 and 2 is narrowed. Here, the second contact surface 1b of the first mass 1 and the first contact surface 2a of the second mass 2 contact the surface 10 of the target object by the rotation of the crank 32. Here, in FIG. 7D, the second contact surface 1b of the first mass 1 and the first contact surface 2a of the second mass 2 completely contact the surface 10 of the target object. As the first and second masses 1 and 2 move to the positions shown in FIG. 7E from FIG. 7D, the second contact surface 1b of the first mass 1 and the first contact surface 2a of the second mass 2 begin to partially contact the surface 10 of the target object and thus the distance between the first mass 1 and the second mass 2 gradually decreases. Accordingly, the second contact surface 1b of the first mass 1 having a relatively weaker frictional force contacts the surface 10 of the target object and simultaneously the first contact surface 2a of the second mass 2 having a relatively stronger frictional force contacts the surface 10 of the target object. Here, since the distance between the first and second masses 1 and 2 decreases, forces to pull the first and second masses 1 and 2 toward the actuator 3 are generated. However, since the first contact surface 1a of the second mass 2 having a relatively stronger frictional force contacts the surface 10 of the target object, the second mass 2 does not move. In contrast, the first mass 1 of which the second contact surface 1b having a relatively weaker frictional force contacts the surface 10 of the target object is moved in one direction, that is, to the right on the drawing sheet, as shown in FIG. 7D.

Figure 7E:
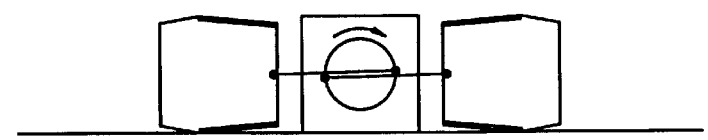

When the crank 32 further rotates clockwise by 90°, thus rotating 360° from the original state, the first and second masses 1 and 2 are disposed as shown in FIG. 7E. The state of FIG. 7E is the same as that of FIG. 7A but the micro robot has moved a predetermined distance by the operation of the actuator 3. As the first and second masses 1 and 2 are moved to the positions shown in FIG. 7E from the positions of FIG. 7D, the distance between the first mass 1 and the second mass 2 gradually decreases. Here, since the first contact surface 2a of the second mass 2 is still in contact with the surface 10 of the target object, the second contact surface 1b of the first mass 1 having a relatively weaker frictional force contacts the surface 10 of the target object and is continuously moved, thus becoming the state shown in FIG. 7E.

As described above, the micro robot according to the present invention can move as the distance between the first mass 1 and the second mass 2 and the frictional forces between the masses 1 and 2 and the surface 10 of the target object change periodically. The same actions are performed by the inverse rotation of the crank 32 so that the micro robot moves in the opposite direction.

In the above preferred embodiment, the first contact surfaces 1a and 2a and the second contact surfaces 1b and 2b are provided at the upper and lower surfaces of each of the first and second masses 1 and 2. This enables the micro robot to move when it is turned over. Of course, the contact surfaces may be formed only at one side of the masses 1 and 2. Also, the positions of the first contact surfaces 1a and 2a and the second contact surfaces 1b and 2b can be switched in the first and second masses 1 and 2. Accordingly, the direction of movement of the micro robot due to the rotation of the crank 32 of the actuator 3 can be changed.

In the actuator 3 as above, the horizontal and vertical movements of the crank 32 can be turned by using a typical well-known motor. The weight of each of the first and second masses 1 and 2 should be determined in relation with the frictional coefficient between each of the first and second contact surfaces 1a, 2a, 1b, and 2b and the surface 10 of the target object since the weight is directly proportional to the frictional force.

<Experiment example>

A micro robot having the above structure according to the present invention was manufactured with the following specifications.

1. Specifications of parts

The whole system: 6.142 g (6.440 g when wires for a motor are included)

First mass: 2.034 g (width×length×the maximum height: 10×10×10.6 mm$^3$)

Second mass: 2.031 g (width×length×the maximum height: 10×10×10.6 mm$^3$)

Actuator: 0.929 g (crank: 0.252 g, arm: 0.121 g)

The entire length when compressed: 32 mm

The entire length when expanded: 44 mm

2. Motor

The type of motor: brushless micro motor

Torque of motor: 7.5 $\mu$Nm

Maximum current: 0.15A at 12V

Gear ratio: 47:1

Torque after speed change (crank torque): 300 $\mu$Nm (Energy efficiency: 50%)

Crank 2 axes stroke: 6 mm

To test the performance of the micro robot having the above specifications, the motor is driven at 75.6 RPM (1.26 revolutions per second) on an over head projector film in the state in which rubber to increase friction is attached to the first contact surface so that the first contact surface has a high frictional coefficient. As a result, the maximum speed of moving forward and backward in a horizontal state is 9.3 mm/sec, the maximum climbing angle 15.79°, and the slip rate is 0.615. Here, the power consumption is about 3W (12V and 0.23A). As a result, the maximum climbing angle is 15.78° on the OHP film while the motor rotates 1.26 revolutions per second, and the minimum power consumption is 1.25W (7.38V and 0.17A)

As described above, the micro robot according to the present invention can move by the change in the distance between the masses of the micro robot together with the periodic change in friction between each of the masses and the surface of the object on which the micro robot moves, instead of wheels or caterpillar tracks. Thus, a power source can be protected by the protective cover. Also, the proceeding speed and direction can be adjusted by the speed and direction of rotation of the motor.

The miniaturization of the present micro robot is possible so that it can be used in medicine or industry.

It is noted that the present invention is not limited to the preferred embodiment described above, and it is apparent that variations and modifications by those skilled in the art can be effected within the spirit and scope of the present invention defined in the appended claims.

What is claimed is:

1. A robot comprising:
first and second masses, each having a first contact surface having a first frictional coefficient and a second contact surface having a second frictional coefficient and formed to be inclined by a predetermined angle with respect to the first contact surface, the first and second contact surfaces being formed at the lower portion of the mass corresponding to a surface of a target object; and
an actuator provided between the first and second masses for periodically changing the distance between the first and second masses and enabling the first and second contact surfaces of the first and second masses to selectively contact the surface of the target object in synchronization with a periodic change in distance between the first and second masses.

2. The robot as claimed in claim 1, wherein each of the first and second masses has four side surfaces and the first and second contact surfaces are provided at the lower portion of each of the first and second masses.

3. The robot as claimed in claim 2, wherein the first frictional coefficient is higher than the second frictional coefficient, and the first contact surfaces of the first and second masses each having the first frictional coefficient are arranged close to the actuator while the second contact surfaces of the first and second masses are arranged next to the first contact surfaces and farther out from the actuator.

4. The robot as claimed in claim 3, wherein the actuator comprises:
a motor;
a crank having first and second crank portions located at opposite sides of the center of rotation along arbitrary axes parallel to each other;
first and second arms rotatably connected to the first and second crank portions of the crank and fixedly coupled to the surfaces of the first and second masses facing the actuator; and
a plurality of gears transferring power of the motor.

5. The robot as claimed in claim 2, wherein a protective cover for protecting the actuator is provided between the first and second masses.

6. The robot as claimed in claim 2, wherein the actuator comprises:
a motor;
a crank having first and second crank portions located at opposite sides of the center of rotation along arbitrary axes parallel to each other;
first and second arms rotatably connected to the first and second crank portions of the crank and fixedly coupled to surfaces of the first and second masses facing the actuator; and
a plurality of gears transferring power of the motor.

7. The robot as claimed in claim 1, wherein each of the first and second masses has four side surfaces and the first and second contact surfaces are provided at both the upper and lower portions of each of the first and second masses.

8. The robot as claimed in claim 7, wherein the first frictional coefficient is higher than the second frictional coefficient, and the first contact surfaces of the first and second masses each having the first frictional coefficient are arranged close to the actuator while the second contact surfaces of the first and second masses are arranged next to the first contact surfaces and farther out from the actuator.

9. The robot as claimed in claim 8, wherein the actuator comprises:
a motor;
a crank having first and second crank portions located at opposite sides of the center of rotation along arbitrary axes parallel to each other;
first and second arms rotatably connected to the first and second crank portions of the crank and fixedly coupled to the surfaces of the first and second masses facing the actuator; and
a plurality of gears transferring power of the motor.

10. The robot as claimed in claim 7, wherein the actuator comprises: a motor;
a crank having first and second crank portions located at opposite sides of the center of rotation along arbitrary axes parallel to each other;
first and second arms rotatably connected to the first and second crank portions of the crank and fixedly coupled to surfaces of the first and second masses facing the actuator; and
a plurality of gears transferring power of the motor.

11. The robot as claimed in claim 7, wherein a protective cover for protecting the actuator is provided between the first and second masses.

12. The robot as claimed in claim 1, wherein the first frictional coefficient is higher than the second frictional coefficient, and the first contact surfaces of the first and second masses each having the first frictional coefficient are arranged close to the actuator while the second contact surfaces of the first and second masses are arranged next to the first contact surfaces and farther out from the actuator.

13. The robot as claimed in claim 12, wherein the actuator comprises:
a motor;
a crank having first and second crank portions located at opposite sides of the center of rotation along arbitrary axes parallel to each other;
first and second arms rotatably connected to the first and second crank portions of the crank and fixedly coupled to the surfaces of the first and second masses facing the actuator; and
a plurality of gears transferring power of the motor.

14. The robot as claimed in claim 12, wherein a protective cover for protecting the actuator is provided between the first and second masses.

15. The robot as claimed in claim 1, wherein the actuator comprises:
a motor;
a crank having first and second crank portions located at opposite sides of the center of rotation along arbitrary axes parallel to each other;
first and second arms rotatably connected to the first and second crank portions of the crank and fixedly coupled to surfaces of the first and second masses facing the actuator; and
a plurality of gears transferring power of the motor.

16. The robot as claimed in claim 15, wherein a protective cover for protecting the actuator is provided between the first and second masses.

17. The robot as claimed in claim 4, wherein a protective cover for protecting the actuator is provided between the first and second masses.

18. The robot as claimed in claim 1, wherein said robot is a micro robot dimensioned to be placed in intestines of a human.

* * * * *